United States Patent
Orosz, Jr.

(10) Patent No.: US 6,716,192 B1
(45) Date of Patent: *Apr. 6, 2004

(54) MEDICAL NEEDLE HAVING A VISIBLY MARKED TIP

(75) Inventor: Steven J. Orosz, Jr., Oregon, OH (US)

(73) Assignee: Charles F. Schroeder, Sylvania, OH (US); part interest ( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 809 days.

(21) Appl. No.: 08/940,601

(22) Filed: Sep. 30, 1997

(51) Int. Cl.$^7$ .............................. A61M 5/00; A61M 5/32
(52) U.S. Cl. ...................... 604/117; 604/187; 604/272; 606/576
(58) Field of Search ................. 604/115–117, 187–189, 604/181, 239, 264, 272, 118; 600/573, 576, 413, 414, 424, 462, 429; 128/917, 919; 606/130

(56) References Cited

U.S. PATENT DOCUMENTS

| | | | | |
|---|---|---|---|---|
| 3,470,011 A | * | 9/1969 | Szumski et al. | |
| 3,906,930 A | * | 9/1975 | Guerra | |
| 4,178,941 A | * | 12/1979 | Raitto | 128/763 |
| 4,256,120 A | * | 3/1981 | Finley | |
| 4,637,838 A | * | 1/1987 | Rausch et al. | 148/6.15 Z |
| 4,638,584 A | * | 1/1987 | Lindsay | 43/17.6 |
| 4,645,491 A | * | 2/1987 | Evans | 604/158 |
| 4,977,897 A | * | 12/1990 | Hurwitz | 128/763 |
| 4,988,339 A | * | 1/1991 | Vadher | 604/197 |
| 5,178,537 A | * | 1/1993 | Currie | 433/72 |
| 5,192,270 A | * | 3/1993 | Carswell, Jr. | 604/116 |
| 5,306,259 A | * | 4/1994 | Fischell et al. | 604/239 |
| 5,312,351 A | * | 5/1994 | Gerrone | 604/117 |
| 5,409,004 A | * | 4/1995 | Sloan | 128/657 |
| 5,484,422 A | * | 1/1996 | Sloane, Jr. et al. | 604/272 |
| 5,571,147 A | * | 11/1996 | Sluijer et al. | 607/99 |
| 5,611,778 A | * | 3/1997 | Brinon | 604/117 |
| 5,695,466 A | * | 12/1997 | Lopez et al. | 604/93 |
| 5,871,834 A | * | 2/1999 | Wang | 428/141 |
| 5,921,971 A | * | 7/1999 | Agro et al. | 604/280 |

OTHER PUBLICATIONS

Becton Dickenson Product Catalog, 1993, p. F–2, Mar. 30, 1993.*

* cited by examiner

Primary Examiner—Angela D. Sykes
Assistant Examiner—Patricia Blanco

(57) ABSTRACT

A medical needle for withdrawal of blood from a patient or for insertion in medicinal containers in which the end of a needle extending from the body of a syringe is provided with one or more marks at its end region to indicate the depth of penetration of the needle below the skin surface of a patient in a given site so that the depth of penetration can be indicated as well as the degree of withdrawal of the needle in such instances as when the needle is required to be partially pulled out maneuvered below the skin to seek an artery for withdrawal of blood. In addition, the end of the needle is provided with coloring and a marking such that it is more visible than the bare stainless steel needles of conventional type thereby assisting in prevention of accidental needle sticks in either the technician or the patient.

5 Claims, 2 Drawing Sheets

MEDICAL NEEDLE HAVING A VISIBLY MARKED TIP

BACKGROUND

The present invention is a medical needle such as an arterial blood gas sampling needle extending from a syringe, having its tip or distal end visibly marked for increased safety of patients and healthcare persons, as well as for improved economics in the care of patients.

In a fair number of incidents a needle intended to be inserted into an artery by a healthcare technician does not hit the mark. In such cases the needle is required to be withdrawn and reinserted, but in the process the original needle upon complete withdrawal from the patient, sanitary practice dictates that the needle not be used over again and must be discarded as waste. In such instances if the needle is withdrawn only in part, and not completely from the area of insertion, it can be guided under the patient's skin to reach the artery successfully.

Such a technique of movement under the skin for arterial puncture must be done carefully and does not allow a large margin of error. Redirectioning of the needle below the skin must be done gently if an initial attempt fails to enter the artery. The needle must be withdrawn almost to the skin surface before redirecting it to avoid tearing of underlying tissue.

A problem arises, however, that while the needle is being withdrawn it is very difficult to determine how close the tip is to the surface in the underlying tissue. The result is that the needle is usually completely withdrawn from the skin and a new needle kit be opened for use. This requires additional time to place pressure on the puncture site until bleeding ceases and re-prep of skin at a new puncture site for reinsertion of the needle. This develops a possible additional chance for infection at the new puncture site as well as causing additional pain to the patient. To reduce such possibilities the needle is retained below the skin surface by withdrawing it up to near the surface of the skin as far as possible without actually withdrawing it from the skin.

Therefore an object of the invention is to provide means indicating when an inserted needle is near the surface of the skin during withdrawal to avoid undesired complete withdrawal from the skin.

Also in the use of such needles their tips are frequently difficult to see and accidental needle sticks occur not too infrequently to both the patient and caretaker technician because of the poor visibility of the metallic body of the needle, and especially the tip.

Another object of the invention therefore is to make the needle tips more visible to reduce the chances of accidental sticks in users, patients and other persons.

In acupuncture practice as another area of healthcare, it is important to know how deep needles are in treatment sites. Further, it can be said generally that the invention is useful in any procedure in which a needle is inserted in a patient.

BRIEF SUMMARY OF THE INVENTION

According to the disclosed invention, the tip of the needle is provided with a highly visible marking such as a black tip or can be pigmented with an esthetic non-threatening bright color, such as orange, yellow or green, so that the tip is more visible than its usual stainless steel body and sharply pointed patient insertion end. In this regard it is also conceived that the entire body of the needle can be colored in contrast to the normal color of flesh of patients. Even in such cases, however, dependent upon use, it would likely be desired that the tip be provided a different color than the body to indicate the zone to be avoided against accidental sticks.

Regardless of the color of the body of the needle, according to the present invention, the tip is provided a contrasting color extending for a distance, for example of three to four millimeters up the shaft, so that as it is pulled back after insertion into the skin of a patient, the color near the tip becomes visible before emergence from the skin. The technician or caretaker is thus alerted as to how close the tip of the needle is to the surface. Complete pullback or withdrawal of the needle from the skin thus becomes unnecessary allowing safe redirection and avoiding cutting of tissue, and eliminating the costly need for use of another needle kit.

The invention also embodies the concept of a needle with two colors at its tip, one at the extreme tip with contrasting color to prevent accident finger sticks and another color just above the extreme end to indicate the length of the tip remaining between the skin. The colors can be provided on the needle in the form such as a ring or a band to indicate upon withdrawal or pull out that the extreme or distal end is near and that further withdrawal can be halted if desired. The mark can also be in the form of a series of visible circumferential bands or grooves in the needle near its tip to provide a graduated indication of the distance to the tip.

DESCRIPTION OF THE PREFERRED EMBODIMENTS

Figure 1:
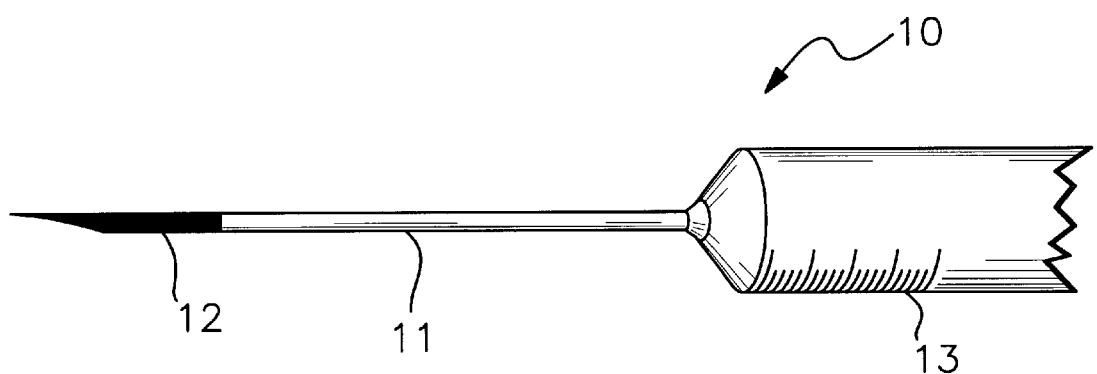
FIG. 1 is an illustration of a portion of a syringe with a needle extending therefrom with a marking for a short length of the needle according to the present invention.

FIG. 1 illustrates a syringe assembly 10 for which portion of a barrel 13 is illustrated from which a needle 11 extends for insertion into the artery of a patient to withdraw blood for test purposes. The end of the needle 11 is provided with a marking, such as colored mark 12 extending back on the body of the needle a few millimeters from the end to make the needle tip more clearly visible under different lighting conditions to assist in preventing accidental sticks into either the technician or the patient from whom the blood is to be withdrawn. A mark 12 can be any of a number of different colors such as black, yellow, green or orange, and in this respect can be made of iridescent matter or formed of fluorescent or phosphorescent matter which will glow more directly in florescent light such as is often found in hospital surgery environments. The tip color is preferably one which is palatable and pleasing rather than appear threatening.

Figure 2:
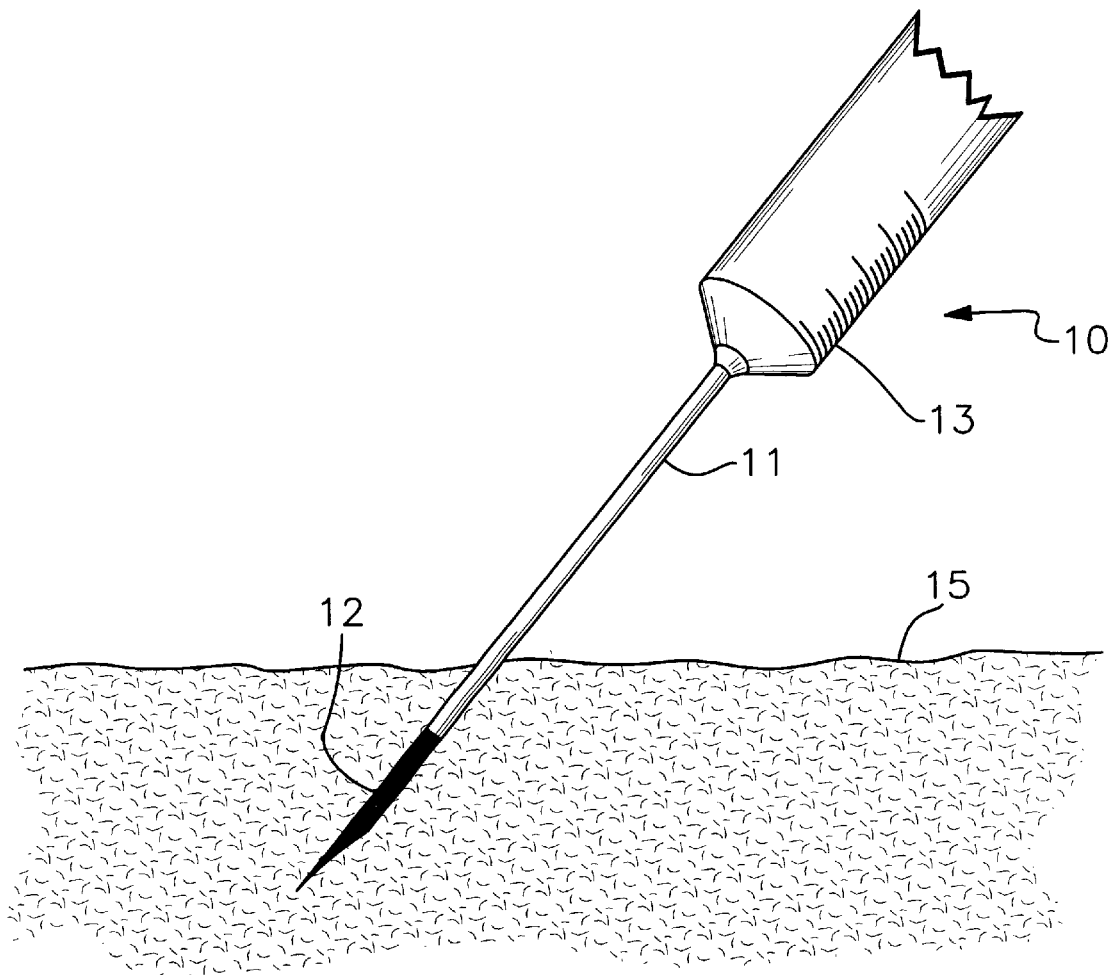
FIG. 2 is an illustration of the syringe of FIG. 1 extending into the skin of a patient with the marking at its end completely submerged.

FIG. 2 illustrates the syringe assembly 10 of FIG. 1 in which the needle 11 extends from the barrel of the syringe 13 with the needle tip extending below the surface of the skin 15 of the patient illustrating how the marked end 12 is completely submerged below the skin surface.

Figure 3:
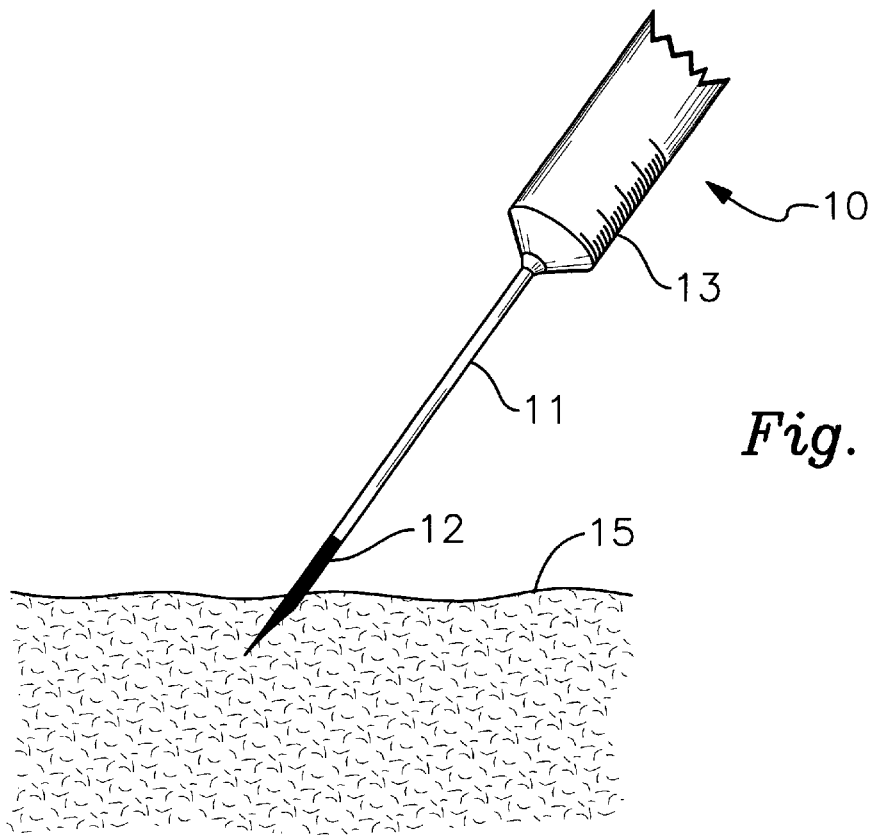
FIG. 3 is an illustration of the syringe of FIG. 2 with the needle partially withdrawn to expose a portion of the marking at the end of the needle without fully withdrawing the needle.

FIG. 3 is another view of the needle and syringe assembly 10 of FIG. 2 in which the needle 11 is partially pulled back illustrating the marking 12 at the end of the needle partially exposed to indicate the degree to which the needle has been pulled out from below the skin 15 of the patient. In such position the partially withdrawn needle can be reinserted to seek another contact with an artery in the event the first insertion is a miss of the artery. Thus the needle need not be completely pulled from below the skin surface to make a successful hit of an artery. If completely pulled out, a new needle must be used in an attempt to effect a successful hit and the first assembly must be disposed of as waste.

Figure 4:
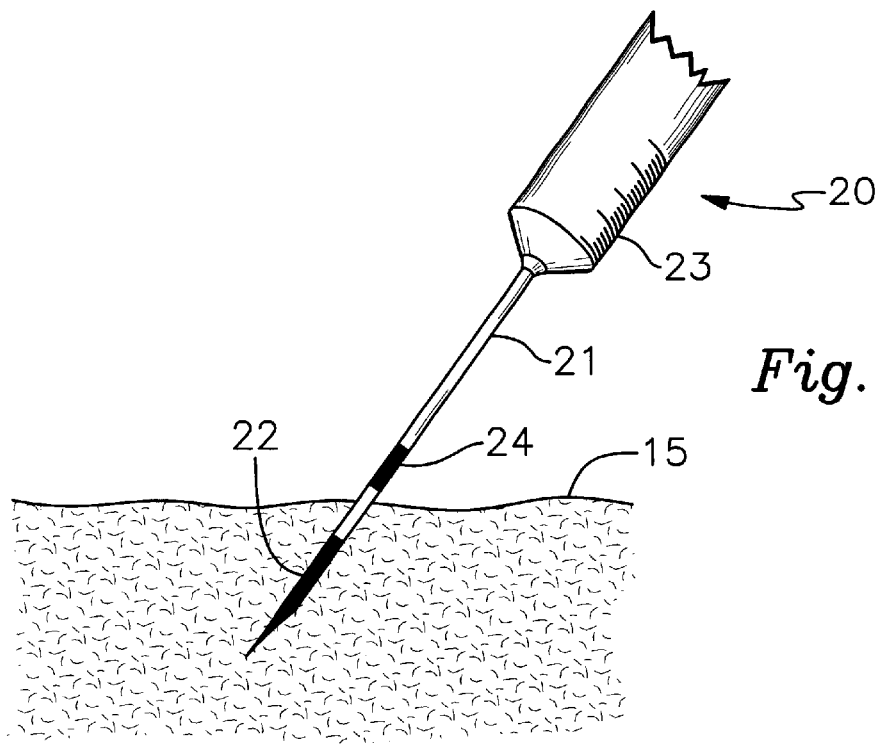
FIG. 4 is an illustration of a portion of a syringe with a needle extending therefrom with the extreme end submerged within the flesh of a patient but partially withdrawn to expose a secondary or limiting mark above the marking at the extreme end of the needle.

FIG. 4 is a illustration of another embodiment of the invention in which a syringe assembly 20 having a barrel 23 and a needle 21 extending therefrom is provided with two marks near the end of the needle. The mark 22 at the extreme end is completely submerged to below the surface of the skin 15 of a patient while the secondary or limit mark 24 illustrates the needle partially withdrawn, and the degree to which it is withdrawn prior to further penetration in an attempt to seek an artery for blood withdrawal.

As an extension of the concept of this embodiment, a series of marks can be provided as graduations along the length of the needle to indicate the degree to which it is inserted below the patient's skin surface. Still further in this regard, the coloring of the end of the needle can be graded in different shades to provide indication of the depth of penetration of the needle or the degree of withdrawal in the event that a second or third redirectioning is necessary to seek a patient's artery. As another use, the color of the tip can be selected for greater visibility for insertion into a sealed container for medication in which instance the insertion zone on the container can be selected to be in a color contrasting that of the needle tip. Needles with marked tips and with distance graduated tips also provide an advantage in the practice of acupuncture where the depth of insertion of needles in the patient is important.

In view of the foregoing, it will be understood that many variations of the arrangement of my invention can be provided within the broad scope of principles embodied therein. Thus, while particular preferred embodiments of my invention have been shown and described, it is intended by the appended claims to cover all such modifications which fall within the true spirit and scope of the invention.

What is claimed is:

1. A medical needle of the type usually combined with a syringe for withdrawal of blood from a patient comprising a longitudinal needle body extending to a sharp tipped insertion end, said sharp end having a distinctly risible marking to facilitate accuracy of use and with minimum possibility of accidental sticks in the user add proximate persons, said marking being a color mark at said end different from the color of said body, said color mark being an iridescent color.

2. A medical needle of the type usually combined with a syringe for withdrawal of blood from a patient comprising a longitudinal needle body extending to a sharp tipped insertion end, said sharp end having a distinctly visible marking to facilitate accuracy of use and with minimum possibility of accidental sticks in the user and proximate persons, said mark being formed of fluorescent matter.

3. A medical needle of the type usually combined with a syringe for withdrawal of blood from a patient comprising a longitudinal needle body extending to a sharp tipped insertion end, said sharp end having a distinctly visible marking to facilitate accuracy of use and with minimum possibility of accidental sticks in the user and proximate persons, said mark being formed of phosphorescent matter.

4. In a process of withdrawing blood from a patient with a syringe and needle assembly the method of inserting said needle into the patient comprising inserting the tip of the needle into the skin of the patient in the vicinity of an artery and directing it to said artery, providing a color mark surrounding the tip of said needle to facilitate accurate directioning of said needle toward said artery in the insertion site and inserting said needle into said artery.

5. In the process set forth in claim 4 wherein in the event the artery is missed pulling the needle partially out of the patient until said mark at the tip is partially visible, maneuvering said needle tip inserted into the skin carefully below the surface of the skin in said insertion site and redirecting said needle tip for said insertion into said artery.

* * * * *